United States Patent
Das et al.

(10) Patent No.: US 12,097,186 B2
(45) Date of Patent: *Sep. 24, 2024

(54) TOPICAL ANALGESIC COMPOSITIONS

(71) Applicant: Bayer HealthCare LLC, Indianola, PA (US)

(72) Inventors: Debanjan Das, Morristown, NJ (US); Emanuel Vizzotti, Millburn, NJ (US); Thomas Dann, Palm Harbor, FL (US); Renee Nelson, Brandon, FL (US); Courtney C. Haynes, Dunedin, FL (US); Soundarya Vaithianathan, Parsippany, NJ (US); Reginald Bradley, Bedminster, NJ (US); Reinhard Walter, Morristown, NJ (US); Gerard Meisel, Budd Lake, NJ (US)

(73) Assignee: Bayer HealthCare LLC, Indianola, PA (US)

( * ) Notice: Subject to any disclaimer, the term of this patent is extended or adjusted under 35 U.S.C. 154(b) by 405 days.

This patent is subject to a terminal disclaimer.

(21) Appl. No.: 16/856,363

(22) Filed: Apr. 23, 2020

(65) Prior Publication Data

US 2020/0345696 A1    Nov. 5, 2020

Related U.S. Application Data

(60) Provisional application No. 62/841,091, filed on Apr. 30, 2019.

(51) Int. Cl.
| | | |
|---|---|---|
| *A61K 31/277* | (2006.01) | |
| *A61K 31/045* | (2006.01) | |
| *A61K 31/125* | (2006.01) | |
| *A61K 31/4164* | (2006.01) | |
| *A61K 47/44* | (2017.01) | |

(52) U.S. Cl.
CPC ........ *A61K 31/4164* (2013.01); *A61K 31/045* (2013.01); *A61K 31/125* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 4,316,887 A | 2/1982 | Kamishita et al. | |
| 5,124,320 A | 6/1992 | Ivy et al. | |
| 5,725,874 A | 3/1998 | Oda et al. | |
| 6,328,982 B1 | 12/2001 | Shiroyama et al. | |
| 6,350,785 B2 | 2/2002 | Gehlsen | |
| 6,524,594 B1 | 2/2003 | Santora et al. | |
| 6,730,288 B1 | 5/2004 | Abram | |
| 6,780,443 B1 | 8/2004 | Nakatsu et al. | |
| 6,890,567 B2 | 5/2005 | Nakatsu et al. | |
| 6,899,901 B2 | 5/2005 | Nakatsu et al. | |
| 7,820,177 B2 | 10/2010 | Kruse et al. | |
| 7,829,099 B2 | 11/2010 | Woeller et al. | |
| 8,039,011 B2 | 10/2011 | Flugge-Berendes et al. | |
| 8,496,950 B2 | 7/2013 | Sorge et al. | |
| 8,568,795 B2 | 10/2013 | Sigurjonsson et al. | |
| 8,685,381 B2 | 4/2014 | Schlessinger et al. | |
| 8,846,063 B2 | 9/2014 | Seidling et al. | |
| 8,900,554 B2 | 12/2014 | Tamarkin et al. | |
| 9,320,705 B2 | 4/2016 | Tamarkin et al. | |
| 9,345,255 B2 | 5/2016 | Kindel et al. | |
| 9,364,402 B1 | 6/2016 | Garcia et al. | |
| 9,597,282 B2 | 3/2017 | Pagliuca et al. | |
| 9,603,817 B2 | 3/2017 | Bean et al. | |
| 9,642,792 B2 | 5/2017 | Tatsuguchi et al. | |
| 10,010,572 B2 | 7/2018 | Parris | |
| 10,117,812 B2 | 11/2018 | Tamarkin et al. | |
| 10,494,330 B2 | 12/2019 | Itoh et al. | |
| 10,576,047 B2 | 3/2020 | Maniar | |
| 2006/0269500 A1 | 11/2006 | Riemer et al. | |
| 2014/0086857 A1 | 3/2014 | Blizzard | |
| 2014/0348959 A1 | 11/2014 | Mitchnick et al. | |
| 2015/0119369 A1 | 4/2015 | Harrison et al. | |
| 2015/0141389 A1 | 5/2015 | Aliyar et al. | |
| 2016/0106690 A1 | 4/2016 | Bucks et al. | |
| 2016/0220475 A1 | 8/2016 | Scherner et al. | |
| 2017/0071874 A1 | 3/2017 | Aranki | |
| 2017/0274084 A1 | 9/2017 | Friedman et al. | |

(Continued)

FOREIGN PATENT DOCUMENTS

| | | | |
|---|---|---|---|
| CN | 105998199 A | 10/2016 | |
| CN | 109481659 A | 3/2019 | |

(Continued)

OTHER PUBLICATIONS

"International Search Report & Written Oinion from corresponding PCT Application PCT/US2020/029485 mailed Jul. 21, 2020".
Andersson H.; et. al., "Activation by Menthol, Icilin, and Cold is Differentially Modulated by Intracellular pH", The Journal of Neuroscience, Jun. 9, 2004, 24 / 23, 5364-5369.
Andrade E.L.; et. al., "TRPA1 Antagonists as Potential Analgesic Drugs", Pharmacology & Therapeutics, 2012, 133, 189-204.
"Anhydrous Gel: Fast absorption, Reduced Gloss, Vitamin C Stabilization", Dow Corning Corporation, 2016.

(Continued)

*Primary Examiner* — Layla Soroush
(74) *Attorney, Agent, or Firm* — Gale Wesley Starkey (57) ABSTRACT

Provided are topical analgesic compositions and methods of preparing topical analgesic compositions comprising a stable nano-encapsulating matrix film. The topical analgesic compositions and methods of preparing topical analgesic compositions may be suited for roll-on applicators. Topical analgesic compositions may include 12 to 16 wt. % menthol; 4 to 8 wt. % camphor; 2 to 15 wt. % film-forming polymer; and 50 to 70 wt. % solvent. To be used in a roll-on applicator, the topical analgesic composition has a viscosity from 800 to 1400 centipoise.

18 Claims, 2 Drawing Sheets

(56) References Cited

U.S. PATENT DOCUMENTS

| | | | |
|---|---|---|---|
| 2017/0348418 | A1 | 12/2017 | Tamarkin et al. |
| 2018/0042832 | A1 | 2/2018 | Kalem et al. |
| 2018/0185429 | A1 | 7/2018 | Iyer |
| 2018/0311184 | A1 | 11/2018 | Hoag |
| 2018/0311274 | A1 | 11/2018 | Majhi |
| 2019/0022000 | A1 | 1/2019 | Tamarkin et al. |
| 2019/0029958 | A1 | 1/2019 | Tamarkin et al. |
| 2019/0046438 | A1 | 2/2019 | Hnat |
| 2019/0076339 | A1 | 3/2019 | Tamarkin et al. |
| 2019/0142710 | A1 | 5/2019 | Hedren et al. |
| 2019/0209442 | A1 | 7/2019 | Syed et al. |
| 2019/0343116 | A1 | 11/2019 | Fuoco |

FOREIGN PATENT DOCUMENTS

| | | | |
|---|---|---|---|
| EP | 0698393 | A1 | 2/1996 |
| EP | 0988852 | A2 | 3/2000 |
| EP | 1066827 | A2 | 1/2001 |
| EP | 1019024 | B1 | 1/2004 |
| EP | 1393716 | A2 | 3/2004 |
| EP | 1947934 | A2 | 7/2008 |
| EP | 2457555 | A2 | 5/2012 |
| EP | 2061432 | B1 | 12/2012 |
| EP | 2101819 | B1 | 1/2013 |
| EP | 1583566 | B1 | 2/2013 |
| EP | 2620137 | A1 | 7/2013 |
| EP | 1556009 | B1 | 12/2014 |
| EP | 2841106 | A1 | 3/2015 |
| EP | 2928450 | A1 | 10/2015 |
| EP | 1699433 | B1 | 5/2017 |
| EP | 2928451 | B1 | 7/2017 |
| EP | 3211061 | A1 | 8/2017 |
| EP | 3219303 | A1 | 9/2017 |
| GB | 1042529 | A | 9/1966 |
| WO | 2007056491 | A2 | 5/2007 |
| WO | 2011014850 | A2 | 2/2011 |
| WO | 2015079233 | A1 | 6/2015 |
| WO | 2018085535 | A2 | 5/2018 |
| WO | 2019014380 | A1 | 1/2019 |
| WO | 2019170195 | A1 | 9/2019 |
| WO | 2019178360 | A1 | 9/2019 |

OTHER PUBLICATIONS

Barkin; Robert L., "The Pharmacology of Topical Analgesics", Postgraduate Medicine, Jul. 2013, 125/4, 7-18.

Biswal B.; et. al., "Formulation and Evaluation of Microemulsion Based Topical Hydrogel Containing Lornoxicam", Journal of Applied Pharmaceutical Science, Dec. 2014, 4/12, 77-84.

Choudhury H.; et. al., "Recent Update on Nanoemulgel as Topical Drug Delivery System", Journal of Pharmaceutical Sciences, Elsevier, Apr. 12, 2017, 106, 1736-1751.

"Cutaneous Sensory Systems", Elsevier, 2012, 321-331.

De Cassia Da Silveira E Sa R.; et. al., "A Review on Anti-Inflammatory Activity of Monoterpenes", Molecules, Jan. 18, 2013, 18, 1227-1254.

Draelos Z.D.; Md., "Botanicals as Topical Agents", Clinics in Dermatology, Elsevier, Copyright 2001, 19, 474-477.

Frederiksen K; et. al., "Formulation considerations in the design of topical, polymeric film-forming systems for sustained drug delivery to the skin", European Journal of Pharmaceutics and Biopharmaceutics, Jan. 14, 2015, 91, 9-15.

Galeotti N.; et. al., "Menthol: a natural analgesic compound", Neuroscience Letters, Elsevier, 2002, 322, 145-148.

Hayman M.; et. al., "Capsaicin: A review of its pharmacology and clinical applications", Current Anaesthesia & Critical Care, Elsevier, 2008, 19, 338-343.

Kathe K.; et. al., "Film Forming Systems for Topical and Transdermal Drug Delivery", Asian Journal of Pharmaceutical Sciences, 2017, 1-11.

Kumar; S., "The Importance of Antioxidant and Their Role in Pharmaceutial Science—A Review", Asian Journal of Research in Chemistry and Pharmaceutical Sciences, 2014, 1/1, 27-44.

Leffingwell; J.C., "Cooling Ingredients and Their Mechanism of Action", Cosmetic Science and Technology, 2009, 661-675.

McCurdy C.R.; et. al., "Analgesic Substances Derived from Natural Products (natureceuticals)", Life Sciences, 2005, 78, 476-484.

Park B; et. al., "Cooling the Skin: Understanding a Specific Cutaneous Thermosensation", Journal of Lifestyle Medicine, Sep. 2013, vol. 3/No. 2, 91-97.

Shirai T.; et. al., "Identification of a Novel TRPM8 Agonist from Nutmeg: A Promising Cooling Compound", ACS Medicinal Chemistry Letters, May 31, 2017, 8, 715-719.

Siyeon K.; et. al., "L-Menthol Attenuates the Magnitude of Cold-induced Vasodilation on the Extremities of Young Females", Journal of Physiological Anthropology, May 9, 2018, 37 / 14, 1-8.

"Takasago Sensates", Lipo Chemicals, 2003.

"Trends and Formulation Strategies for Topical Drugs", Pharmaceutical Technology, BASF, May 2018, 1-36.

Turek C.; et. al., "Stability of Essential Oils: A Review", Comprehensive Reviews in Food Science and Food Safety, 2013, 12, 40-53.

Watson; P., "Topical Capsaicin as an Adjuvant Analgesic", Journal of Pain and Symptom Management, Oct. 7, 1994, 9, 425-433.

Webster G.; et. al., "Selection of Pharmaceutical Antioxidants by Hydrodynamic Voltammetry", Electroanalysis, Apr. 7, 2012, 24 / 6, 1394-1400.

TOPICAL ANALGESIC COMPOSITIONS

FIELD OF THE INVENTION

This relates to topical analgesic compositions, and more particularly, to topical analgesic compositions designed for roll-on application and having a high payload of active ingredient(s).

BACKGROUND OF THE INVENTION

Topical analgesics are often used to help treat musculoskeletal injuries and disorders, including pulled muscles, sprained muscles, and arthritis. Some formulations of topical analgesics provide warming or cooling sensation in the area of application. When applied to an area of discomfort on the skin, the active ingredient(s) in the topical analgesic react to produce a cool feeling, and then a warm feeling on the surface of the skin. Muscles proximate to the cooling/warming sensation send signals to area nerve receptors. These signals are sent from the nerve receptors to the nerve fibers until they reach the brain. Thus, when a patient applies a topical analgesic to an area of pain, the cooling/warming sensations of the topical analgesic distract the brain from any pain signals it may be receiving from that same area of the skin. This in turn distracts the patient from his or her aches or pains.

SUMMARY OF THE INVENTION

Provided are topical analgesic compositions for roll-on application and methods for preparing topical analgesic compositions for roll-on application. In particular, topical analgesics for roll-on application as provided herein are designed for an easy, clean application, a sustained delivery of active ingredient(s) to the skin, and have a high payload of active ingredient(s).

Conventional topical analgesics known in the art are typically provided as a gel product in a tube packaging. To apply the topical analgesic provided in a tube, a user is required to squeeze the tube to expel some of the product, and apply onto the skin using their hands. However, topical analgesics tend to be sticky and messy products. Thus, applying such conventional topical analgesics onto the skin is neither an easy nor a clean process. Additionally, conventional topical analgesics are typically rubbed or washed away earlier than desired. This requires a user to apply the conventional topical analgesic again, which can be inconvenient and time-consuming. Furthermore, conventional topical analgesic compositions have a relatively low payload of active ingredients. As discussed in more detail below, actives such as menthol and camphor have low solubility in typical solvents, preventing a high payload of menthol and/or camphor to be mixed into the conventional formulations.

Accordingly, provided herein are topical analgesic compositions designed for roll-on application that allow for easy, clean application, sustained delivery of active ingredient(s) on the skin, as well as a relatively high payload of active ingredient(s). For example, roll-on topical analgesic compositions according to embodiments provided herein are easier and cleaner to apply than conventional topical analgesics discussed above. By using a roll-on applicator to apply the topical analgesic composition onto the skin, a user doesn't need to get his or her hand to apply the topical analgesic composition.

Once applied to a user's skin, topical analgesic compositions for roll-on application provided herein develop an encapsulating matrix in the form of a film layer on the skin. In particular, once the primary solvent of the product evaporates, a film layer is formed on the area of application. The film layer comprises an encapsulating matrix that traps fragments or deposits of the active ingredients. This encapsulating matrix is caused by a phase change of the specific solvent system where the polymers are de-solubilized once the formulation is applied on the skin, which is described in more detail below. The combination of the encapsulating matrix and the polymer system achieves sustained delivery of actives on the skin by adhering to the area of application and being wash or rub-resistant.

Additionally, topical analgesic compositions provided herein include a relatively high payload of menthol and camphor. Menthol and camphor individually have low solubility in common solvents used in conventional roll-on formulas (e.g., a mixture of predominantly water with some alcohol). However, by using alcohol as a solvent, a solubilizing agent, and one or more film-forming polymers, a relatively high payload of menthol and camphor (i.e., 21 wt. % or greater) has been achieved in the topical analgesic compositions disclosed.

In some embodiments, a topical analgesic composition is provided, the topical analgesic composition comprising: 12 to 16 wt. % menthol; 4 to 8 wt. % camphor; 2 to 15 wt. % film-forming polymer; and 50 to 70 wt. % solvent, wherein the topical analgesic composition has a viscosity from 800 to 1400 centipoise.

In some embodiments of the topical analgesic composition, the topical analgesic composition comprises 0.025 to 0.250 wt. % histamine dihydrochloride.

In some embodiments of the topical analgesic composition, the amount of menthol and the amount of camphor comprises 21 wt. % or more.

In some embodiments of the topical analgesic composition, the topical analgesic composition has a pH from 6.0 to 7.0.

In some embodiments of the topical analgesic composition, the topical analgesic composition has a specific gravity from 0.7 to 1.0.

In some embodiments of the topical analgesic composition, the 2 to 25 wt. % film-forming polymer comprises one or more of hydroxypropyl cellulose, a terpolymer of vinylpyrrolidone, vinyl caprolactum and dimethylaminoethyl methacrylate, and a terpolymer of poly(isobutylene-alt-maleic anhydride), dimethylaminopropylamine, and methoxy-PEG/PPG-31/9-2-propylamine.

In some embodiments of the topical analgesic composition, the 10 to 20 wt. % menthol and the 5-10 wt. % camphor form a eutectic mixture.

In some embodiments of the topical analgesic composition, the topical analgesic composition comprises 1.5 to 9 wt. % sensate.

In some embodiments of the topical analgesic composition, the sensate includes one or more of menthoxypropanediol, isopulegol, and vanillyl butyl ether.

In some embodiments of the topical analgesic composition, the topical analgesic composition comprises 0.5 to 3.0 wt. % of one or more essential oils.

In some embodiments of the topical analgesic composition, the one or more essential oils comprises one or more of peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil, and frankincense (*Olibanum* or *Boswellia carterii*) oil.

In some embodiments of the topical analgesic composition, the topical analgesic composition comprises 0.1 to 5 wt. % linseed oil.

In some embodiments of the topical analgesic composition, the topical analgeisic composition comprises 0.5 to 3.0 wt. % fragrance.

In some embodiments of the topical analgesic composition, the solvent comprises an alcohol.

In some embodiments of the topical analgesic composition, the topical analgesic composition comprises droplets having an average droplet size of 500 to 1500 nanometers.

In some embodiments, a method for treating muscle and joint ache or pain is provided, the method comprising administering to a patient in need thereof a topical analgesic composition according to any one of the topical analgesic composition embodiments.

In some embodiments, a roll-on topical analgesic product is provided, the topical analgesic product comprising: a roll-on applicator; and a topical analgesic composition comprising: 12 to 16 wt. % menthol; 4 to 8 wt. % camphor; 2 to 15 wt. % film-forming polymer; and 50 to 70 wt. % solvent, wherein the topical analgesic composition has a viscosity from 800 to 1400 centipoise contained within the roll-on applicator to form a roll-on topical analgesic product.

In some embodiments of the topical analgesic product, the topical analgesic composition comprises 0.025 to 0.250 wt. % histamine dihydrochloride.

In some embodiments of the topical analgesic composition, the amount of menthol and the amount of camphor comprises 21 wt. % or more.

In some embodiments of the topical analgesic composition, the topical analgesic composition has a pH from 6.0 to 7.0.

In some embodiments of the topical analgesic composition, the topical analgesic composition has a specific gravity from 0.7 to 1.0.

In some embodiments of the topical analgesic composition, the 2 to 25 wt. % film-forming polymer comprises one or more of hydroxypropyl cellulose, a terpolymer of vinylpyrrolidone, vinyl caprolactum and dimethylaminoethyl methacrylate, and a terpolymer of poly(isobutylene-alt-maleic anhydride), dimethylaminopropylamine, and methoxy-PEG/PPG-31/9-2-propylamine.

In some embodiments of the topical analgesic composition, the 10 to 20 wt. % menthol and the 5-10 wt. % camphor form a eutectic mixture.

In some embodiments of the topical analgesic composition, the topical analgesic composition comprises 1.5 to 9 wt. % sensate.

In some embodiments of the topical analgesic composition, the sensate includes one or more of menthoxypropanediol, isopulegol, and vanillyl butyl ether.

In some embodiments of the topical analgesic composition, the topical analgesic composition comprises 0.5 to 3.0 wt. % of one or more essential oils.

In some embodiments of the topical analgesic composition, the one or more essential oils comprises one or more of peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil, and frankincense (*Olibanum* or *Boswellia carterii*) oil.

In some embodiments of the topical analgesic composition, the topical analgesic composition comprises 0.1 to 5 wt. % linseed oil.

In some embodiments of the topical analgesic composition, the topical analgesic composition comprises 0.5 to 3.0 wt. % fragrance.

In some embodiments of the topical analgesic composition, the solvent comprises an alcohol.

In some embodiments of the topical analgesic composition, the topical analgesic composition comprises droplets having an average droplet size of 500 to 1500 nanometers.

In some embodiments, a method of preparing a topical analgesic composition is provided, the method comprising: preparing a mixture comprising menthol and camphor; and adding a solvent and a film-forming polymer to the mixture comprising menthol and camphor to form a topical analgesic composition.

In some embodiments of the method of preparing a topical analgesic composition, preparing a mixture comprising menthol and camphor comprises preparing a eutectic mixture comprising menthol and camphor.

In some embodiments of the method of preparing a topical analgesic composition, the method comprises adding histamine dihydrochloride to the mixture comprising menthol and camphor.

In some embodiments of the method of preparing a topical analgesic composition, the method comprises adding a sensate to the mixture comprising menthol and camphor.

In some embodiments of the method of preparing a topical analgesic composition, adding a sensate to the mixture comprising menthol and camphor comprises adding one or more of menthoxypropanediol, isopulegol, and vanillyl butyl ether to the mixture comprising menthol and camphor.

In some embodiments of the method of preparing a topical analgesic composition, the method comprises adding one or more essential oils to the mixture comprising menthol and camphor.

In some embodiments of the method of preparing a topical analgesic composition, comprising adding one or more essential oils to the mixture comprising menthol and camphor comprises adding one or more of peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil, and frankincense (*Olibanum* or *Boswellia carterii*) oil to the mixture comprising menthol and camphor.

In some embodiments of the method of preparing a topical analgesic composition, the topical analgesic composition comprises 10 to 20 wt. % menthol.

In some embodiments of the method of preparing a topical analgesic composition, the topical analgesic composition comprises 5 to 10 wt. % camphor.

In some embodiments of the method of preparing a topical analgesic composition, the topical analgesic composition comprises 2 to 15 wt. % film-forming polymer.

In some embodiments of the method of preparing a topical analgesic composition, the topical analgesic composition comprises 50 to 70 wt. % solvent.

In some embodiments of the method of preparing a topical analgesic composition, the topical analgesic composition has a viscosity from 800 to 1400 centipoise.

In some embodiments of the method of preparing a topical analgesic composition, the topical analgesic composition has a specific gravity of 800 to 1400.

In some embodiments of the method of preparing a topical analgesic composition, the topical analgesic composition has a pH of 6.0-7.0.

In some embodiments of the method of preparing a topical analgesic composition, the topical analgesic composition comprises droplets having an average droplet size of 500 to 1500 nanometers.

BRIEF DESCRIPTION OF THE DRAWINGS

Various embodiments are described with reference to the accompanying figure, in which.

DETAILED DESCRIPTION OF THE INVENTION

Described herein are topical analgesic compositions for roll-on applicators and methods of making topical analgesic compositions for roll-on applicators. As described above, conventional topical analgesic compositions are messy to apply and have relatively low payloads of menthol and/or camphor. However, topical analgesic compositions according to embodiments provided herein are formulated to be applied to a user with a roll-on applicator. By applying the topical analgesic composition using a roll-on applicator, a user can enjoy an easier and cleaner application process. Additionally, topical analgesic compositions described herein can provide sustained delivery of actives on the skin and can include a higher payload of menthol and camphor than conventional topical analgesic compositions and conventional topical analgesic compositions for roll-on applicators.

As mentioned above, topical analgesic compositions provided herein can provide sustained delivery of actives on a user's skin as compared to conventional topical analgesic compositions. Specifically, topical analgesic compositions provided herein use a polymer system to generate an encapsulating matrix, instead of a conventional core-shell type encapsulation system. Conventional core-shell type encapsulation systems are difficult to manufacture and stabilize in alcohol systems. Specifically, conventional core-shell type encapsulating systems include micro-capsules which require being premade, isolated, purified, stabilized, and then added to the main formulation. These numerous processing steps increase costs and manufacturing challenges. Further, conventional core-shell type encapsulating systems cannot deliver sustained benefits because the formulations tend to wash or rub off the skin.

Figure 1:
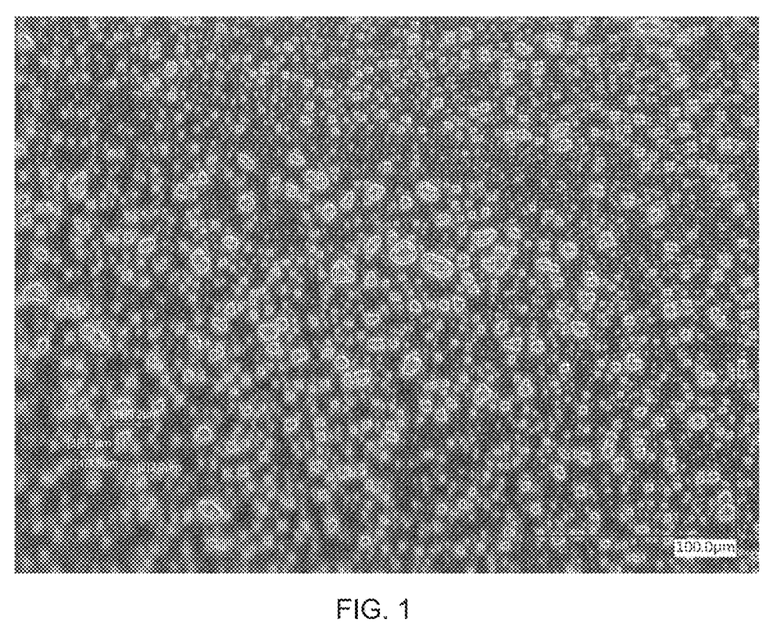
FIG. 1 provides an image of microscopic encapsulated actives formed by phase change, according to some embodiments.

However, topical analgesic compositions provided herein use a polymer system to form an encapsulating matrix that can provide sustained delivery of active ingredient(s) on a user's skin. In some embodiments, topical analgesic compositions can form a film on a user's skin once applied by developing in situ a film-forming, encapsulating matrix on the surface of the skin. Once the solvent (e.g., alcohol) of a topical analgesic composition has evaporated, an encapsulating matrix film remains on the skin. This encapsulating film matrix entraps the active(s) in tiny fragments or deposits on the surface of the skin. This phenomenon is illustrated in FIG. 1. Specifically, FIG. 1 shows microscopic encapsulated active(s) formed by phase change.

In some embodiments, the encapsulating matrix film develops due to the combination of a unique polymer system and a phase change phenomenon. The particular polymer system is explained in detail below. This polymer system is soluble in alcohol and can remain solubilized in the alcohol along with the active(s). Once a topical analgesic composition is applied to the skin, the solvent (i.e., alcohol) evaporates. Simultaneously, the topical analgesic composition is exposed to moisture present on the skin and moisture produced by the skin. Thus, the topical analgesic applied on the skin changes from an alcohol-based composition to a water-based composition. In some embodiments, because the polymer system is less soluble in water than in alcohol (i.e., the polymer system is hydrophobic), it forms a film, encapsulating the active(s). This encapsulating matrix can hold, or localize, the active(s) at the area of application to provide sustained delivery or a prolonged benefit to the area of skin. The encapsulating matrix is also wash-resistant.

Figure 2:
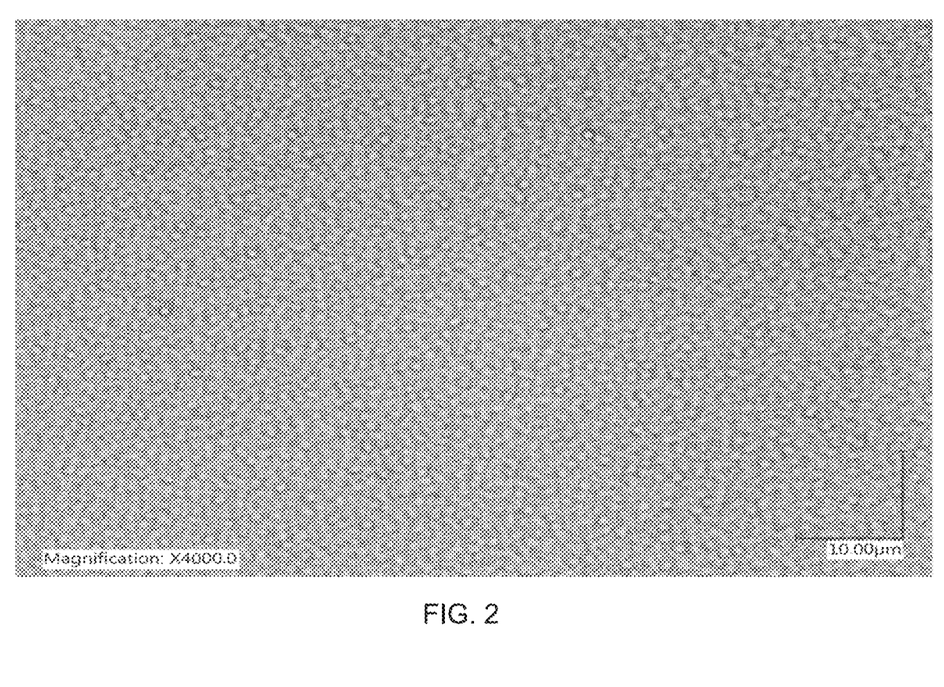
FIG. 2 provides a magnified image of a topical analgesic composition, according to some embodiments.
Figure 3:
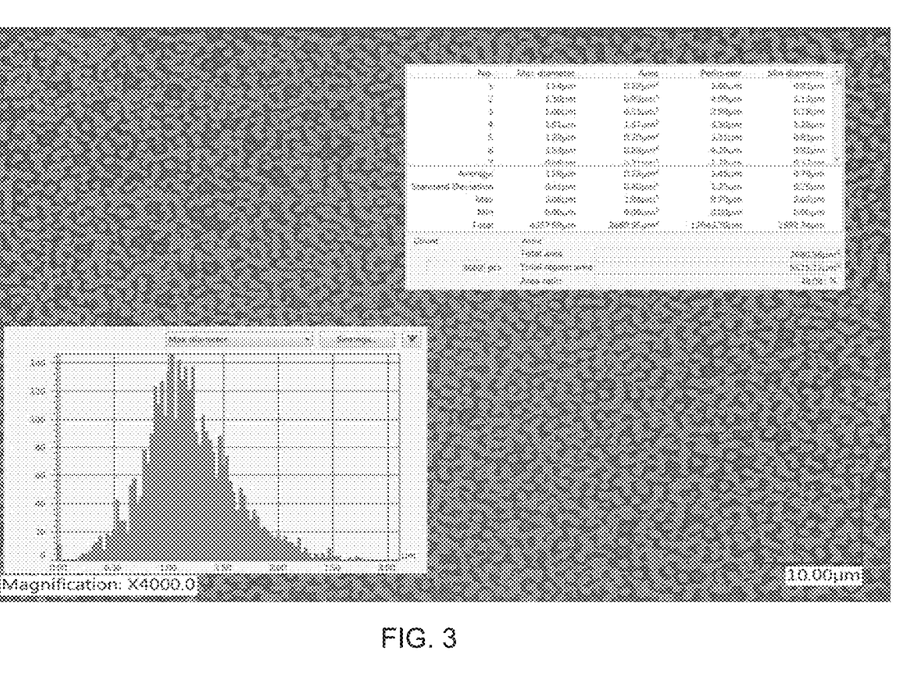
FIG. 3 provides droplet size data of a topical analgesic composition, according to some embodiments.

As water exchange across the surface of the skin continues over time (i.e., transepithelial water loss), the polymer system slowly breaks down, releasing the active ingredients into the skin. Accordingly, topical analgesic compositions provided herein can carry a high active load of active ingredients (e.g., menthol, camphor) by encapsulating the actives in nano-sized droplets that can achieve slow and sustained release into the skin. FIGS. 2 and 3, which are described in more detail below, show microscopic images of topical analgesic compositions provided herein.

Additionally, topical analgesic compositions for roll-on applicator according to embodiments provided herein may include both menthol and camphor. The combination of menthol and camphor can produce an oily eutectic mixture which can have a limited solubility in most solvents commonly used in topical analgesics (and specifically topical analgesic compositions for roll-on applicators). However, in some embodiments, topical analgesic compositions can include a high payload of up to 35 wt. % menthol-camphor solution. This can be achieved by using a combination of ethanol as the primary solvent, a solubilizing agent, and a specific mixture of other polymers, discussed in more detail below.

Provided below is a discussion of topical analgesic compositions, topical analgesic compositions as provided in a roll-on applicator, and methods for preparing topical analgesic compositions.

Topical Analgesic Compositions

Provided below is a discussion of topical analgesic compositions according to some embodiments. In some embodiments, a topical analgesic composition can include an active ingredient (e.g., menthol, camphor), a film-forming and/or a bioadhesive polymer, a solubilizing agent, a sensate, an anti-tacking agent, an antioxidant, a fragrance, and/or a solvent.

In some embodiments, topical analgesic compositions can comprise an organoleptic composition. An organoleptic composition may comprise cooling and warming sensates, an essential oil mixture comprising one or more essential oils, vitamin E, linseed oil, and optionally also further excipients. Organoleptic compositions provided herein can add to the sensation of long-lasting pain-relieving effect, to provide a pleasant fragrance as a mask, and/or to complement the natural scent of menthol and camphor. Organoleptic compositions are described in detail further below.

Active Ingredients

Numerous different active ingredients may be used in the topical analgesic compositions provided herein. Menthol and/or camphor may be used, as discussed above. In addition, histamine dihydrochloride, capsaicin, methyl salicylate, methyl nicotinate may also be used in some embodiments. When applied topically, histamine dihydrochloride can temporarily reduce the pain associated with the musculoskeletal system. Topical analgesic compositions provided herein may include menthol, camphor, histamine dihydrochloride, capsaicin, methyl salicylate, and/or methyl nicotinate.

In some embodiments, a roll-on topical analgesic may include menthol. Menthol can be naturally obtained from the oils of corn mint, peppermint, and other mints or can be obtained as a synthetic product. Menthol is commonly used in topical analgesics because it has local anesthetic (i.e., a medication that causes the absence of pain sensations) and counterirritant (i.e., a substance that creates irritation or mild inflammation in one location to lessen discomfort or inflammation in a second location) properties. If the concentration of menthol in a topical analgesic composition is too high, it can cause irritation or chemical burning. If the concentration is too low, the topical analgesic composition may be less effective than desired, or even ineffective at providing a cooling sensation to a user. In some embodiments, a topical analgesic composition may comprise from 3 to 30 wt. %, from 5 to 25 wt. %, or from 10 to 20 wt. % menthol. In some embodiments, a topical analgesic composition may comprise less than 30 wt. %, less than 25 wt. %, less than 20 wt. %, less than 15 wt. %, less than 10 wt. %, or less than 5 wt. % menthol. In some embodiments, a topical analgesic composition may comprise more than 3 wt. %, more than 5 wt. %, more than 10 wt. %, more than 15 wt. %, more than 20 wt. %, or more than 25 wt. % menthol.

In some embodiments, a roll-on topical analgesic may include camphor. Camphor is a terpinoid found in the wood of camphor laurel, an evergreen tree, and kapur tree, a timber tree or can be obtained synthetically. Camphor is readily absorbed in the skin and produces a warming sensation when vigorously applied, or a cooling sensation when gently applied. It can also produce a local analgesia effect. Like menthol, it also has counterirritant properties. Topical analgesic compositions comprising high concentrations of camphor may cause skin redness, skin irritations, or chemical burns. Topical analgesic compositions comprising too little camphor may be less effective than desired, or even ineffective at providing a warming sensation to a user. In some embodiments, a topical analgesic composition may comprise from 1 to 20 wt. %, from 3 to 15 wt. %, or from 5 to 10 wt. % camphor. In some embodiments, a topical analgesic may comprise less than 20 wt. %, less than 18 wt. %, less than 15 wt. %, less than 12 wt. %, less than 10 wt. %, less than 8 wt. %, or less than 5 wt. % camphor. In some embodiments, a topical analgesic may comprise more than 3 wt. %, more than 5 wt. %, more than 8 wt. %, more than 10 wt. %, more than 12 wt. %, more than 15 wt. %, or more than 18 wt. % camphor.

In some embodiments, the combination of menthol and camphor can form a eutectic mixture. For example, menthol and camphor combined at certain concentrations or ratios may result in a eutectic mixture. A eutectic mixture is a mixture containing two or more components that has a lower melting point than the separate melting points of its individual constituents. Although menthol and camphor are individually solid at room temperature, the combination of menthol and camphor is known to form liquid, eutectic mixtures at certain ratios. In some embodiments, certain combinations of concentrations of menthol and camphor may be particularly suitable for the topical analgesic compositions as described herein, including, but not limited to, concentrations that result in a eutectic mixture of menthol and camphor. These eutectic mixtures may be more readily formulated than the corresponding non-eutectic compositions, as the liquid phase of the eutectic mixture promotes uniform distribution of the active ingredients throughout the formulation and facilitates absorption into the skin upon application for a rapid pain relieving effect.

In some embodiments, a topical analgesic composition may include from 5 to 35 wt. %, from 15 to 35 wt. %, or from 20 to 35 wt. % menthol-camphor mixture. In some embodiments, a topical analgesic may include more than 5 wt. %, more than 10 wt. %, more than 15 wt. %, more than 20 wt. %, more than 25 wt. %, or more than 30 wt. % menthol-camphor mixture. In some embodiments, a topical analgesic composition may include less than 35 wt. %, less than 30 wt. %, less than 25 wt. %, less than 20 wt. %, less than 15 wt. %, or less than 10 wt. % menthol-camphor mixture. If the menthol-camphor mixture is much greater than 35 wt. %, the mixture may have difficulties mixing into solution with the solvent and other components of topical analgesic compositions provided herein.

Organoleptic Compositions

Organoleptic compositions provided may be incorporated into topical analgesic compositions to add to the sensation of long-lasting pain-relieving effect, to provide a pleasant fragrance as a mask, and/or to complement the natural scent of menthol and camphor. In some embodiments, organoleptic compositions can include cooling and warming sensates, an essential oil mixture, linseed oil, and optionally also further excipients (e.g., vitamin E oil, surfactants, and penetration enhancers) for inclusion in the topical analgesic compositions containing high concentrations of menthol and camphor provided herein.

In some embodiments, an organoleptic composition comprises one or more sensates. One or more sensates may be selected from the group consisting of cooling sensates, warming sensates, and any combinations or mixtures thereof. Suitable cooling and warming sensates may include, but are not limited to, menthol and menthol derivatives (e.g., isomenthol, neomenthol, neoisomenthol, menthoglycol para-menthoxy-3,8-propanediol, isopulegol, menthoxypropanediol), capsaicin, other capsaicinoids (e.g., dihydrocapsaicin, nordihydrocapsaicin, homocapsaicin, and homodihydrocapsaicin), eucalyptol, cinnamaldehyde, vanilloid derivatives such as vanillyl alcohol alkyl ethers (e.g., vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol n-hexyl ether, vanillyl amyl ether, vanillyl alcohol methyl ether, vanillyl alcohol ethyl ether, vanillyl isoamyl ether, vanillyl butyl ether), gingerol, zingerone, shogaol, piperine, icilin, and any combinations thereof. In some embodiments, the organoleptic composition comprises menthoxypropanediol (Coolact® 10), isopulegol (Coolact® P), icilin, or a combination thereof, as cooling sensates. In other embodiments, the organoleptic composition comprises vanillyl butyl ether (Hotact® VBE), cinnamaldehyde, or piperine, or a combination thereof, as warming sensates.

Menthoxypropanediol is a sensate and synthetic derivative of menthol that can provide a cooling sensation when applied to the skin. The compound acts as a cooling agent by stimulating the receptors at the nerve endings of the skin where applied to produce a cooling sensation. Menthoxypropanediol can also be used as a fragrance or a masking ingredient in some formulations. Too much menthoxypropanediol can cause irritation and even chemical burning. Too little menthoxypropanediol in a topical analgesic formulation may render the formulation less effective at producing a cooling sensation. In some embodiments, a topical analgesic composition comprising the organoleptic composition provide herein includes from 2 to 40 wt. %, from 5 to 30 wt. %, or from 10 to 20 wt. % menthoxypropanediol. In some embodiments, an organoleptic composition comprises less than 40 wt. %, less than 35 wt. %, less than 30 wt. %, less than 25 wt. %, less than 20 wt. %, less than 15 wt. %, less than 10 wt. %, or less than 5 wt. % menthoxypropanediol. In some embodiments, an organoleptic composition comprises more than 2 wt. %, more than 5 wt. %, more than 10 wt. %, more than 15 wt. %, more than 20 wt. %, more than 25 wt. %, more than 30 wt. %, or more than 35 wt. % menthoxypropanediol.

Isopulegol is a sensate that is a chemical precursor to menthol. It is a terpene found in cannabis and known for having a minty odor. However, isopulegol also has anxiolytic, gastroprotective, and anticonvulsive properties. When used in the topical analgesic compositions provided herein, isopulegol can be used as a sensate that provides a cooling effect to the skin. It can function as a sensate by directly stimulating the receptors at the nerve endings of the skin to produce a cooling sensation. Specifically, isopulegol can provide a similar cooling effect as menthol, but without the odor of menthol. Topical analgesic compositions having too much isopulegol can be irritating to the skin. However, topical analgesic compositions having too little isopulegol may render the formulation less effective at providing the desired cooling effect. In some embodiments, a topical analgesic composition comprising the organoleptic composition provided herein includes from 2 to 40 wt. %, from 5 to 30 wt. %, or from 10 to 20 wt. % isopulegol. In some embodiments, an organoleptic composition comprises less than 40 wt. %, less than 35 wt. %, less than 30 wt. %, less than 25 wt. %, less than 20 wt. %, less than 15 wt. %, less than 10 wt. %, or less than 5 wt. % isopulegol. In some embodiments, an organoleptic composition comprises more than 2 wt. %, more than 5 wt. %, more than 10 wt. %, more than 15 wt. %, more than 20 wt. %, more than 25 wt. %, more than 30 wt. %, or more than 35 wt. % isopulegol.

Vanillyl butyl ether is a sensate that provides a warming effect when applied to the skin. The warming effect of vanillyl butyl ether can occur immediately upon application, building rapidly within the first five minutes and lasting up to two hours. Compared to active ingredients that can produce a warming effect (e.g., capsaicin or *Capsicum* extract), vanillyl butyl ether can be less irritating. That said, topical analgesic compositions comprising too much vanillyl butyl ether can still cause skin irritation and/or burning. Topical analgesic compositions comprising too little vanillyl butyl ether may render the formulation less effective at providing the desired warming effect. In some embodiments, an organoleptic composition provided herein includes from 0.1 to 15 wt. %, from 1 to 10 wt. %, or from 2 to 5 wt. % vanillyl butyl ether. In some embodiments, an organoleptic composition provide herein includes less than 15 wt. %, less than 10 wt. %, less than 8 wt. %, less than 5 wt. %, less than 3 wt. %, less than 1 wt. %, or less than 0.5 wt. % vanillyl butyl ether. In some embodiments, an organoleptic composition provide herein includes more than 0.1 wt. %, more than 0.5 wt. % more than 1 wt. %, more than 3 wt. %, less than 5 wt. %, more than 8 wt. % or more than 10 wt. % vanillyl butyl ether.

In addition to individual chemical compounds that may provide cooling or warming sensation, the organoleptic composition may also comprise naturally-derived extracts, roots, or resins containing one or more sensates. For example, in some embodiments, the organoleptic composition may comprise chili pepper (*Capsicum frutescens*) resin, ginger root extract and cinnamon *cassia* bark extract, or any combination thereof. Combinations of particular naturally-derived extracts, roots, or resins may also be known and referred to by known trade name(s). For example, Phytol™ Heat is suitable naturally-derived extract, root, and/or resin containing one or more sensates and includes a combination of chili pepper (*Capsicum frutescens*) resin, ginger root extract and cinnamon *cassia* bark extract).

In some embodiments, a complementary cooling effect to supplement the effects of camphor and menthol may be desired. Such complementary cooling effect may be achieved with particular combinations of certain cooling sensates that may be incorporated into the organoleptic composition, and ultimately the topical analgesic compositions. In some embodiments, the one or more sensates are selected from the group consisting of menthoxypropanediol, isopulegol, and icilin, and any combinations thereof.

In some embodiments, a complementary warming sensation is desired to supplement the effects of camphor and menthol. Similar combinations of warming sensates may be incorporated into the organoleptic composition and the topical analgesic compositions to achieve the desired warming sensation. In some embodiments, the one or more sensates are selected from the group consisting of cinnamaldehyde, piperine, and vanillyl butyl ether, and any combinations thereof.

A combined cooling and warming sensation may be desired in some topical analgesic compositions. To achieve a combined cooling and warming sensation, combinations of certain cooling and warming sensates may be incorporated into an organoleptic composition to achieve the mixed cooling/warming effect. In some embodiments, the organoleptic composition comprises one or more sensates selected from the group consisting of menthoxypropanediol, isopulegol, vanillyl butyl ether, a combination of chili pepper (*Capsicum frutescens*) resin, ginger root extract and Cinnamon *cassia* bark extract, and any combinations thereof. In some embodiments, the one or more sensates are selected from the group consisting of menthoxypropanediol, isopulegol, and vanillyl butyl ether, and any combinations thereof. In certain embodiments, the one or more sensates are menthoxypropanediol, isopulegol, and vanillyl butyl ether.

Essential oils may also be included in the organoleptic compositions as described herein to complement the effect of the menthol, camphor, and aforementioned sensates on hot and cold receptors in the skin and to imbue an overall pleasant fragrance to the topical analgesic compositions. In addition to their sensory attributes, the essential oils utilized in organoleptic compositions and/or topical analgesic described herein may further provide anti-inflammatory, anti-oxidant and/or antinociceptive effects on the skin. In some embodiments, the organoleptic composition comprises one or more essential oils. For example, suitable essential oils may include peppermint (*Mentha piperita*) oil, eucalyptus (*Eucalyptus globulus*) oil, rosemary (*Rosmarinus officinalis*) oil, Tunisian rosemary (*Rosmarinus officinalis*) oil, Idaho rosemary (*Rosmarinus officinalis*) oil, clove (*Eugenia caryophyllata*) oil, Spanish marjoram (*Thymus mastichina*) oil, sweet marjoram (*Organum majorana*) oil frankincense (*Olibanum* or *Boswellia carterii*) oil, clove (*Syzygium aromaticum*) oil, Ceylon cinnamon (*Cinnamomum verum* or *zeylanicum*) oil, cardamom (*Elettaria cardamomum*) oil, Guatemalan cardamom (*Elettaria cardamomum*) oil, black pepper (*Piper nigrum*) oil, bay leaf (or bay laurel or *Laurus nobilis*) oil, *cassia* (*Cinnamomum cassia*) oil, ginger (*Zingiber officinale*) oil, Chinese ginger (*Zingiber officinale*) oil, lemongrass Cochin (*Cymbopogon citratus*) oil, fennel (*Foeniculum vulgare*) oil, basil (*Ocimum basilicum*) oil, spearmint (*Mentha spicata* or *cardiaca*) oil, Roman chamomile (*Anthemis nobilis* of *Chamaemelum nobile*) oil, sage (*Salvia officinalis* L.) oil, Spanish sage (*Salvia lavandulaefolia*) oil, clary sage (*Salvia sclarea*) oil, Bulgarian lavender (*Lavandula angustifolia* or *officinalis*) oil, and nutmeg (*Myristica fragrans*) oil.

As described above, combinations of sensates may be prepared to afford a cooling, warming or mixed cooling and warming sensation to the organoleptic composition, and ultimately also to topical analgesic compositions. Similarly, combinations of essential oils in the essential oil mixture may be prepared to supplement the cooling, warming, or mixed cooling and warming effects of the sensates. Certain combinations or blends of essential oils may be especially suitable for providing a cooling sensation and/or a warming sensation as desired. For example, in some embodiments wherein a warming sensation is desired, the essential oil mixture may comprise clove (*Eugenia caryophyllata*) oil, Ceylon cinnamon (*Cinnamomum verum* or *zeylanicum*) oil, cardamom (*Elettaria cardamomum*) oil, black pepper (*Piper nigrum*) oil, bay leaf (or bay laurel or *Laurus nobilis*) oil, cassia (*Cinnamomum cassia*) oil, and/or ginger (*Zingiber officinale*) oil. In other embodiments wherein a cooling sensation is desired, the essential oil mixture may comprise fennel (*Foeniculum vulgare*) oil, peppermint (*Mentha piperita*) oil, basil (*Ocimum basilicum*) oil, spearmint (*Mentha spicata* or *cardiaca*) oil, eucalyptus (*Eucalyptus globulus*) oil, sage (*Salvia officinalis* L.) oil, and/or nutmeg (*Myristica fragrans*) oil. When a mixed cooling and warming sensation is desired, an organoleptic composition may include an essential oil mixture comprising peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil, and/or frankincense (*Olibanum* or *Bosewellia carterii*) oil. It should be recognized the essential oil mixtures tailored for cooling sensation, warming sensation and mixed cooling and warming sensation can be combined with the respective combinations of sensates for cooling, warming and mixed cooling and warming.

Surprisingly, the essential oil mixture comprising peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil, and frankincense (*Olibanum* or *Bosewellia carterii*) oil was discovered to provide a combined cooling and warming sensation. This combination of essential oils can also effectively mask the smell of menthol and camphor and is compatible with a variety of topical analgesic formulations.

In some embodiments, an organoleptic composition comprises from 2 to 40 wt. %, from 5 to 30 wt. %, or from 10 to 20 wt. % essential oil mixture. In some embodiments, an organoleptic composition comprises less than 40 wt. %, less than 35 wt. %, less than 30 wt. %, less than 25 wt. %, less than 20 wt. %, less than 15 wt. %, less than 10 wt. %, or less than 5 wt. % essential oil mixture. In some embodiments, an organoleptic composition comprises more than 2 wt. %, more than 5 wt. %, more than 10 wt. %, more than 15 wt. %, more than 20 wt. %, more than 25 wt. %, more than 30 wt. %, or more than 35 wt. % essential oil mixture.

It should be recognized that in certain embodiments wherein peppermint oil is included in the essential oil mixture, the peppermint oil may contribute to the total quantity of menthol in the overall topical analgesic formulation. As a result of the contribution of menthol from the peppermint oil, which may depend upon the source of the peppermint oil, the fraction of menthol in the peppermint oil and total concentration of the peppermint oil in the topical analgesic, the quantity of menthol added as an independent ingredient may be adjusted accordingly to achieve the desired concentration.

In some embodiments, an organoleptic composition comprises vitamin E. Vitamin E is a known antioxidant and may be included in the essential oil mixture to prevent oxidation of the individual essential oils for longer shelf life. Vitamin E may be included in an organoleptic composition as an antioxidant and emollient, independently of and in addition to any vitamin E already included in the essential oil mixture. Vitamin E broadly refers to a group of fat soluble compounds known as tocopherols and tocotrienols, which have free-radical scavenging properties, but as referred to herein may include any individual isomers (alpha, beta, gamma, delta) of tocopherol and/or tocotrienol, or any combinations thereof. In some embodiments, an organoleptic composition and/or a topical analgesic comprises from 1 to 20 wt. %, from 3 to 15 wt. %, or from 5 to 10 wt. % vitamin E. In some embodiments, an organoleptic composition comprises less than 20 wt. %, less than 15 wt. %, less than 10 wt. %, less than 8 wt. %, less than 5 wt. %, or less than 3 wt. % vitamin E. In some embodiments, an organoleptic composition comprises more than 1 wt. %, more than 3 wt. %, less than 5 wt. %, more than 8 wt. %, more than 10 wt. %, or more than 15 wt. % vitamin E.

Certain relative percentages of the individual essential oils (and vitamin E) may be especially complementary in fragrance and scent. Table 1 below provides one example of a complementary combination of the mixture of essential oils and vitamin E for use with mentholated and camphorated topical formulations. It should be recognized that the individual percentages of each of the essential oils may be varied to provide the desired complementary scent and sensation with respect to the other cooling and/or warming sensates, menthol, and camphor. For example, in some embodiments, the percentages of the essential oils shown in the table below may be varied within ±25%. In addition, it should be further recognized that the exemplary essential oil blend shown in the table below is not intended to be limiting and that the essential oils in the organoleptic composition may be substituted to provide greater cooling or warming effect as desired.

| International Nomenclature of Cosmetic Ingredient | % (with vitamin E) |
|---|---|
| Rosemary (*Rosmarinus officinalis*) leaf oil | 24.5 |
| Spanish marjoram (*Thymus mastichina*) flower oil | 24.5 |
| Peppermint (*Mentha piperita*) oil | 14.5 |
| Eucalyptus (*Eucalyptus globulus*) leaf oil | 14.5 |
| Clove (*Eugenia caryophyllus*) oil | 10.0 |
| Frankincense (*Boswellia carterii*) oil | 10.0 |
| Tocopherol | 2.0 |
| TOTAL | 100.0 |

In some embodiments, the organoleptic composition comprises linseed oil as an emollient. Linseed oil, also known as flaxseed oil or flax oil, contains a variety of triglycerides, including alpha-linoleic acid, which can help to moisturize skin and enhance skin feel of topical formulations. In some embodiments, an organoleptic composition includes from 0.1 to 15 wt. % or from 1 to 5 wt. % linseed oil. In some embodiments, an organoleptic composition includes less than 15 wt. %, less than 10 wt. %, less than 5 wt. %, less than 4 wt. %, less than 3 wt. %, less than 2 wt. %, less than 1 wt. %, less than 0.8 wt. %, less than 0.5 wt. %, less than 0.3 wt. %, less than 0.1 wt. %, or less than 0.05 wt. % linseed oil. In some embodiments, an organoleptic composition includes more than more than 0.1 wt. %, more than 0.3 wt. %, more than 0.5 wt. %, more than 0.8 wt. %, more than 1 wt. %, more than 2 wt. %, more than 3 wt. %, more than 4 wt. %, more than 5 wt. %, or more than 10 wt. % linseed oil.

In some embodiments, the organoleptic composition comprises one or more excipients. For example, one or more excipients may include surfactants and/or penetration enhancers. Suitable surfactants may include, but are not limited to, those derived from functionalization of sorbitan. For example, in some embodiments, the organoleptic composition may comprise sorbitan ester surfactants, ethoxylated sorbitan ester surfactants (polysorbates), or any mixtures thereof. It should be recognized that certain classes of surfactants may be especially useful, including for example, sorbitan ester surfactants, ethoxylated sorbitan ester surfactants (polysorbates), or any mixtures thereof, wherein the ester is moiety is oleate. In certain embodiments, the organoleptic composition comprises surfactants selected from the group consisting of polyethylene glycol sorbitan monooleate, sorbitan monooleate, sorbitan trioleate, and any combination thereof. An example of a suitable polyethylene glycol sorbitan monooleate is Tween® 80. An example of a suitable sorbitan monooleate is Span® 80. An example of a suitable sorbitan trioleate is Span® 85.

In some embodiments, the organoleptic composition comprises a penetration enhancer. In some embodiments, the penetration enhancer may include an alkylene glycol. In still other embodiments, the penetration enhancer comprises pentylene glycol. In some embodiments, an organoleptic composition may include from 5 to 50 wt. %, from 10 to 45 wt. %, or from 20 to 40 wt. % penetration enhancer. In some embodiments, an organoleptic composition may include more than 5 wt. %, more than 10 wt. %, more than 15 wt. %, more than 20 wt. %, more than 25 wt. %, more than 30 wt. %, more than 35 wt. %, more than 40 wt. %, or more than 45 wt. % penetration enhancer. In some embodiments, an organoleptic composition may include less than 50 wt. %, less than 45 wt. %, less than 40 wt. %, less than 35 wt. %, less than 30 wt. %, less than 25 wt. %, less than 20 wt. %, less than 15 wt. %, or less than 10 wt. % penetration enhancer.

As described above, the organoleptic composition containing sensates, essential oils and linseed oil, and optionally also further excipients, may be incorporated into topical formulations possessing high concentrations of menthol and camphor, including the topical analgesics and the topical analgesic compositions of the present disclosure.

Although the organoleptic composition are described herein with specific reference to their use in the topical analgesic compositions of the present disclosure, it should be recognized that the organoleptic composition as described herein may be tailored for incorporation into different formulation types also having high concentrations of menthol and camphor, including emulsions, gels, sprays, etc. It should also be recognized that the organoleptic composition as described herein may be adapted to include varied combinations of the cooling and warming sensates, or varied relative concentrations of the sensates to the essential oil mixture, or even exclude certain or all optional excipients.

Polymer System

In some embodiments, a topical analgesic composition may include one or more polymers. For example, suitable classes of polymers may include film-forming polymers and bioadhesive polymers. A film-forming polymer can create a film on the skin that includes barrier properties, wash and/or sweat resistance, flexibility, etc. As used in the topical analgesic compositions provided herein, film-forming polymers can form a film in situ upon application on a user's skin, enabling an encapsulating matrix that can entrap small deposits of active ingredient(s) to the skin to provide sustained delivery of the topical analgesic.

Suitable film-forming polymers include, but are not limited to, polyvinylpyrrolidones, polyisobutylenes, polyvinyl acetates, polyvinyl alcohols, hydroxypropyl methylcellulose, ethyl cellulose, hydroxypropyl cellulose, chitosan, polymethacrylates, silicones, polydimethylsiloxanes, polyacrylates, polyacrylamindes, polyamides, polyquaterniums, polyurethane-62, trideceth-6, PPG-17/IPDI/DMPA copolymer, AMP-acrylates/allyl methacrylate copolymer, PVM/MA copolymers, acrylates/timethicone copolymer, trimethylsiloxysilicates, silicone acrylates, polyester-5, cellulose acetate butyrate, cellulose acetate propionate and copolymers/combinations thereof.

A bioadhesive polymer is a polymer that provides adhesion to biological tissue. For example, a bioadhesive polymer may adhere to skin, bone, intestinal walls, etc. As used in the topical analgesic compositions provided herein, bioadhesive polymers can work with film-forming polymers to form a film in situ upon application on a user's skin, enabling an encapsulating matrix that can entrap small deposits of active ingredient(s) to the skin. The bioadhesive in particular can help hold the polymeric film to the skin to provide sustained delivery of the topical analgesic. Suitable bioadhesive polymers include, but are not limited to, polyacrylic acids, cyanoacrylates, hydroxypropyl cellulose, gelatin, dextran, acrylonitrile styrene acrylate, sodium alginate, chitin, polyethylene glycol, 2-hydroxy-3-methacryloyloxypropylated carboxymethyl chitin, dextran, poly(alkylcyanoacrylate), poly(lactic acid), poly (amido amine), hyaluronic acid, poly(acrylic acid), polystyrene, cellulose, hydroxypropyl methylcellulose, chitosan, alginate, starches, pectin, rubber, polycaprolactone, and/or any combinations thereof.

A topical analgesic composition including too much film-forming and/or bio-additive polymer can dilute the analgesic properties of the composition. Topical analgesic compositions comprising too little film-forming and/or bio-additive polymer may not be able to sufficiently form the encapsulating matrix that can provide sustained delivery of the active ingredient(s) as discussed above. In some embodiments, topical analgesic compositions provided herein may comprise a polymer system including a terpolymer of vinyl caprolactam, vinylpyrrolidone, and dimethylaminoethyl methacrylate, a copolymer of isobutylene, dimethylaminopropyl maleimide, ethoxylated maleimide, and maleic acid, and hydroxypropyl cellulose. In some embodiments, a topical analgesic composition may include from 1 to 20 wt. %, from 3 to 15 wt. %, or from 5 to 10 wt. % polymer. In some embodiments, a topical analgesic composition may include less than 20 wt. %, less than 18 wt. %, less than 15 wt. %, less than 12 wt. %, less than 10 wt. %, less than 8 wt. %, less than 5 wt. %, or less than 3 wt. % polymer. In some embodiments, a topical analgesic may include more than 1 wt. %, more than 3 wt. %, more than 5 wt. %, more than 8 wt. %, more than 10 wt. %, more than 12 wt. %, more than 15 wt. %, or more than 18 wt. % polymer.

Additional Ingredients

Topical analgesic compositions provided herein may also include ingredients including, but not limited to, a fragrance blend, an emulsifier, and/or a solvent.

In some embodiments, topical analgesic compositions may include a fragrance blend. For example, a fragrance blend may include one or more fragrances including, but not limited to, sage, bergamot, spearmint, lemon, rose, jasmine, lavender, cedar wood, amber, musk, and/or eucalyptus. In some embodiments, a fragrance blend may provide a pleasant fragrance as a mask, and/or to complement the natural scent of menthol and camphor. For example, a fragrance blend may provide a mint effect with soothing qualities and botanical facets. In some embodiments, a topical analgesic composition may include from 0.01 to 10 wt. %, from 0.1 to 5 wt. %, or from 0.5 to 3 wt. % fragrance blend. In some embodiments, a topical analgesic composition includes less than 10 wt. %, less than 8 wt. %, less than 5 wt. %, less than 3 wt. %, less than 1 wt. %, or less than 0.5 wt. % fragrance blend. In some embodiments, the topical analgesic includes more than 0.1 wt. %, more than 0.5 wt. % more than 1 wt. %, more than 3 wt. %, less than 5 wt. %, or more than 8 wt. % fragrance blend.

In some embodiments, a topical analgesic composition may include an emulsifier. An emulsifier can reduce any tackiness or sticky feel caused by oily active(s) and reduce any oily or greasy feel on the skin. Examples of suitable emulsifiers may include volatile silicone fluids having a viscosity of less than 5 m$^2$/s, dimethicone copolyol, and polydimethylsiloxane grafted with either polyethylene glycol and/or polypropylene glycol. A suitable commercially-available emulsifier may include Emulsifier 10 (i.e., lauryl PEG/PPG-18/19 methicone). In some embodiments, a topical analgesic composition may include from 0.1 to 10 wt. %, from 0.5 to 5 wt. %, or from 1 to 3 wt. % emulsifier. In some embodiments, a topical analgesic composition may include more than 0.1 wt. %, more than 0.5 wt. %, more than 1.0 wt. %, more than 1.5 wt. %, more than 2.0 wt. %, more than 2.5 wt. %, more than 3.0 wt. %, more than 3.5 wt. %, more than 4.0 wt. %, more than 5.0 wt. %, more than 6.0 wt. %, more than 7.0 wt. %, or more than 8.0 wt. % emulsifier. In some embodiments, a topical analgesic composition may include less than 8.0 wt. %, less than 7.0 wt. %, less than 6.0 wt. %, less than 5.0 wt. %, less than 4.0 wt. %, less than 3.5 wt. %, less than 3.0 wt. %, less than 2.5 wt. %, less than 2.0 wt. %, less than 1.5 wt. %, or less than 1.0 wt. % emulsifier.

Topical analgesic compositions according to embodiments provided herein may include a solvent. Suitable solvents may include alcohol (e.g., ethanol). In some embodiments, menthol and/or camphor, at certain concentrations, may be more soluble in alcohol than in water-based solvents. For example, a suitable alcohol may include specially denatured alcohol 40-B 190 proof. In some embodiments, a topical analgesic composition may include from 30 to 90 wt. %, from 40 to 80 wt. %, or from 50 to 70 wt. % solvent. In some embodiments, a topical analgesic composition may include less than 90 wt. %, less than 85 wt. %, less than 80 wt. %, less than 75 wt. %, less than 70 wt. %, less than 65 wt. %, less than 60 wt. %, less than 55 wt. %, less than 50 wt. %, less than 45 wt. %, less than 40 wt. %, or less than 35 wt. % solvent. In some embodiments, a topical analgesic composition may include more than 30 wt. %, more than 35 wt. %, more than 40 wt. %, more than 45 wt. %, more than 50 wt. %, more than 55 wt. %, more than 60 wt. %, more than 65 wt. %, more than 70 wt. %, more than 75 wt. %, more than 80 wt. %, or more than 85 wt. % solvent.

Additionally, topical analgesic compositions provided herein may include stable nano-encapsulating matrix film. As described in more detail below, the active ingredients (e.g., menthol, camphor), the sensates, and the essential oils of a topical analgesic composition form small, nano-sized droplets. These nano-sized droplets are dispersed and stabilized in a film-forming matrix comprising the polymer system and the solvent (i.e., alcohol) and can mitigate coalescence. Additionally, the encapsulating film-forming matrix that traps the active ingredients, sensates, and essential oils can lead to faster absorption through the skin and easier spreadability of the topical analgesic composition into the skin. Thus, the small droplet size contributes to beneficial characteristics of the topical analgesic compositions provided herein. In some embodiments, the average droplet size may be from 100 to 4000 nanometers, from 300 to 3000 nanometers, or from 500 to 1500 nanometers. In some embodiments, the average droplet size may be less than 4000 nanometers, less than 3500 nanometers, less than 3000 nanometers, less than 2500 nanometers, less than 2000 nanometers, less than 1500 nanometers, less than 1000 nanometers, less than 800 nanometers, less than 500 nanometers, or less than 300 nanometers. In some embodiments, the average droplet size may be more than 100 nanometers, more than 300 nanometers, more than 500 nanometers, more than 800 nanometers, more than 1000 nanometers, more than 1500 nanometers, more than 2000 nanometers, more than 2500 nanometers, more than 3000 nanometers, or more than 3500 nanometers.

Topical Analgesic Compositions Comprising an Organoleptic Composition

Discussed below are topical analgesic compositions comprising an organoleptic composition as described above. In particular, the compounds/ingredients described below have been introduced with respect to the organoleptic compositions disclosed above and are reiterated below with respect to the topical analgesic composition as a whole. As described in detail above, organoleptic compositions provided herein may be incorporated into topical analgesic compositions to add to the sensation of long-lasting pain-relieving effect, to provide a pleasant fragrance as a mask, and/or to complement the natural scent of menthol and camphor. An organoleptic composition according to embodiments provided herein may include cooling and warming sensates, an essential oil mixture, linseed oil, and optionally also further excipients (such as vitamin E oil, surfactants, penetration enhancers). In some embodiments, a topical analgesic composition may include from 1 to 30 wt. %, from 2 to 20 wt. %, or from 3 to 10 wt. % organoleptic composition. In some embodiments, a topical analgesic composition may include more than 1 wt. %, more than 2 wt. %, more than 3 wt. %, more than 5 wt. %, more than 8 wt. %, more than 10 wt. %, more than 15 wt. %, more than 20 wt. %, or more than 25 wt. % organoleptic composition. In some embodiments, a topical analgesic composition may include less than 30 wt. %, less than 25 wt. %, less than 20 wt. %, less than 15 wt. %, less than 10 wt. %, less than 8 wt. %, less than 5 wt. %, less than 3 wt. %, or less than 2 wt. % organoleptic composition.

In some embodiments, a topical analgesic composition comprising the organoleptic composition provide herein may include one or more sensates including, but not limited to, menthoxypropanediol, isopulegol, and vanillyl butyl ether, and any combination thereof.

As discussed above, menthoxypropanediol is a sensate that can provide a cooling sensation to the skin. In some embodiments, a topical analgesic composition comprising the organoleptic composition provided herein includes from 0.01 to 10 wt. %, from 0.1 to 5 wt. %, or from 0.5 to 3 wt. % menthoxypropanediol. In some embodiments, a topical analgesic composition comprising the organoleptic composition provide herein includes less than 10 wt. %, less than 8 wt. %, less than 5 wt. %, less than 3 wt. %, less than 1 wt. %, or less than 0.5 wt. % menthoxypropanediol. In some embodiments, a topical analgesic composition comprising the organoleptic composition provide herein includes more than 0.1 wt. %, more than 0.5 wt. % more than 1 wt. %, more than 3 wt. %, less than 5 wt. %, or more than 8 wt. % menthoxypropanediol. An example of a commercially-available menthoxypropanediol is Coolact® 10.

As discussed above, isopulegol is a sensate that can provide a cooling effect on the skin. In some embodiments, a topical analgesic composition comprising the organoleptic composition provided herein includes from 0.01 to 10 wt. %, from 0.1 to 5 wt. %, or from 0.5 to 3 wt. % isopulegol. In some embodiments, a topical analgesic composition comprising the organoleptic composition provide herein includes less than 10 wt. %, less than 8 wt. %, less than 5 wt. %, less than 3 wt. %, less than 1 wt. %, or less than 0.5 wt. % isopulegol. In some embodiments, a topical analgesic composition comprising the organoleptic composition provide herein includes more than 0.1 wt. %, more than 0.5 wt. % more than 1 wt. %, more than 3 wt. %, less than 5 wt. %, or more than 8 wt. % isopulegol. An example of a commercially-available isopulegol includes Coolact® P.

As described in detail above, vanillyl butyl ether is a sensate that can provide a warming sensation on the skin. In some embodiments, a topical analgesic composition comprising the organoleptic composition provided herein includes from 0.01 to 10 wt. %, from 0.1 to 5 wt. %, or from 0.5 to 3 wt. % vanillyl butyl ether. In some embodiments, a topical analgesic composition comprising the organoleptic composition provide herein includes less than 10 wt. %, less than 8 wt. %, less than 5 wt. %, less than 3 wt. %, less than 1 wt. %, or less than 0.5 wt. % vanillyl butyl ether. In some embodiments, a topical analgesic composition comprising the organoleptic composition provide herein includes more than 0.1 wt. %, more than 0.5 wt. % more than 1 wt. %, more than 3 wt. %, less than 5 wt. %, or more than 8 wt. % vanillyl butyl ether. An example of a commercially-available vanillyl butyl ether is Hotact® VBE.

In some embodiments, a topical analgesic composition comprising the organoleptic composition provided herein includes an essential oil mixture comprising one or more essential oils and/or vitamin E. Essential oils can provide a more pleasant sensory experience for a user by complementing and/or masking the odors of menthol and/or camphor. Vitamin E, when applied to the skin, can be moisturizing and can help protect the skin from free radical damage. In some embodiments, the essential oil mixture can include one or more of peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil and frankincense (*Olibanum* or *Boswellia carterii*) oil, and/or vitamin E. In some embodiments, a topical analgesic composition comprising the organoleptic composition provided herein comprises from 0.01 to 10 wt. %, from 0.1 to 5 wt. %, or from 0.5 to 3 wt. % essential oil mixture. In some embodiments, a topical analgesic composition comprising the organoleptic composition provide herein includes less than 10 wt. %, less than 8 wt. %, less than 5 wt. %, less than 3 wt. %, less than 1 wt. %, or less than 0.5 wt. % essential oil mixture. In some embodiments, the topical analgesic includes more than 0.1 wt. %, more than 0.5 wt. % more than 1 wt. %, more than 3 wt. %, less than 5 wt. %, or more than 8 wt. % essential oil mixture.

In some embodiments, a topical analgesic composition comprising the organoleptic composition provided herein includes linseed oil. A topical analgesic composition comprising the organoleptic composition provided herein may include from 0.1 to 5 wt. % linseed oil. In some embodiments, a topical analgesic composition comprising the organoleptic composition provide herein can include less than 5 wt. %, less than 4 wt. %, less than 3 wt. %, less than 2 wt. %, less than 1 wt. %, less than 0.8 wt. %, less than 0.5 wt. %, less than 0.3 wt. %, less than 0.1 wt. %, or less than 0.05 wt. % linseed oil. In some embodiments, a topical analgesic composition comprising the organoleptic composition provide herein may include more than 0.01 wt. %, more than 0.05 wt. %, more than 0.1 wt. %, more than 0.3 wt. %, more than 0.5 wt. %, more than 0.8 wt. %, more than 1 wt. %, more than 2 wt. %, more than 3 wt. %, or more than 4 wt. % linseed oil.

Roll-on Applicator and Methods of Preparing Topical Analgesic Compositions

Provided below is a discussion of roll-on applicators for topical analgesics and method of preparing and using topical analgesic compositions according to the embodiments provided herein.

Roll-On Applicator

As described above, conventional topical analgesics can be messy for a user to apply to their skin. However, by using a roll-on applicator according to embodiments provided herein, a user may apply the topical analgesic to their skin using the roller ball of the roll-on applicator. This application technique prevents a user from having to use their hand to apply and/or spread the topical analgesic across an area of their skin, getting their hand sticky in the process.

However, to be compatible with a roll-on dispenser, achieving a particular viscosity of the topical analgesic composition is beneficial. In some embodiments, the viscosity of the topical analgesic composition may be from 400 to 2000 centipoise (cps), from 500 to 1800 cps, or from 600 to 1600 cps. In some embodiments, the viscosity of a topical analgesic composition may be more than 400 cps, more than 500 cps, more than 600 cps, more than 800 cps, more than 1000 cps, more than 1200 cps, more than 1400 cps, or more than 1800 cps. In some embodiments, the viscosity of a topical analgesic composition may be less than 2000 cps, less than 1800 cps, less than 1600 cps, less than 1400 cps, less than 1200 cps, less than 1000 cps, less than 800 cps, less than 600 cps, or less than 500 cps.

Other beneficial properties of the topical analgesic composition include specific gravity and pH. In some embodiments, the density of the topical analgesic composition may be from 0.2 to 2.0, from 0.4 to 1.5, or from 0.6 to 1.2. In some embodiments, the density may be greater than 0.2, greater than 0.4, greater than 0.6, greater than 0.8, greater than 1.0, greater than 1.2, greater than 1.4, or greater than 1.6. In some embodiments, the density may be less than 2.0, less than 1.8, less than 1.6, less than 1.4, less than 1.2, less than 1.0, less than 0.8, less than 0.6, or less than 0.4.

In some embodiments, the pH may be from 4.0 to 9.0, from 4.5 to 8.5, or from 5.0 to 8.0. In some embodiments, the pH may be greater than 4.0, greater than 4.5, greater than 5.0, greater than 5.5, greater than 6.0, greater than 6.5, greater than 7.0, or greater than 7.5. In some embodiments, the pH may be less than 9.0, less than 8.5, less than 8.0, less than 7.5, less than 7.0, less than 6.5, less than 6.0, less than 5.5, or less than 5.0. In some embodiments, pH may be measured as an apparent pH in a non-aqueous system.

Methods of Preparing Topical Analgesic Compositions

Provided herein are methods of preparing topical analgesic compositions according to embodiments provided herein.

In some embodiments, a menthol/camphor melt can be prepared. In particular, the menthol and/or camphor can be heated in a water bath at a temperature from 30 to 50° C. or from 35 to 45° C. In some embodiments, the temperature may be more than 30° C., more than 35° C., or more than 40° C. In some embodiments, the temperature may be less than 50° C., less than 45° C., or less than 40° C. The menthol and/or camphor may be heated until melted into a colorless liquid, at which time the melt may be removed from the heat.

In some embodiments, camphor may be dissolved in room temperature alcohol. The camphor and alcohol may be combined in a side-phase vessel. The menthol may be added to the camphor solution. In some embodiments, the menthol may be added to the camphor and alcohol solution such that $T_{m,\ menthol} < T_{addition} \leq 40°$ C. The menthol, camphor, alcohol solution may then be added to a main batch vessel.

In some embodiments, camphor may be dissolved in room temperature alcohol. The camphor and alcohol may be combined in a side-phase vessel. The menthol may be held at $T_{m,\ menthol} < T_{addition} \leq 40°$ C. In some embodiments, the menthol and camphor solution may be added to a main batch vessel separately.

In some embodiments, histamine dihydrochloride (if used) may be mixed into the solvent. The histamine dihydrochloride and solvent may be mixed using a suitable mixer. For example, a suitable mixer may include those provided by IKA Laboratory Equipment. Using side sweeps and/or a homogenizer, the histamine dihydrochloride may dissolute into the solvent.

In some embodiments, one or more polymers may be added to the mixer containing the solvent solution prior to adding the menthol and/or camphor. For example, hydroxypropyl cellulose may be added at this step. The one or more polymer may be mixed into the solvent until the solution is visibly clear and no particulate matter remains.

In some embodiments, the menthol and/or camphor may be added to the mixer. If the menthol and/or camphor melt has begun recrystallizing, the melt may be reheated prior to adding to the mixer. The menthol and/or camphor melt may be added and mixed with the components of steps two and three until a visibly clear solution is achieved.

In some embodiments, one or more polymers may be added to the mixer (i.e., in addition to any polymer(s) that was added in a previous step. For example, a vinyl caprolactam/VP/dimethylaminoethyl methacrylate copolymer and/or a polyimidie-1 may be added to the mixer. The one or more polymers may be mixed with side sweeps until the contents are uniform. A homogenizer may optionally be used.

The remaining ingredients of the topical analgesic may be added to the mixer and mixed until uniform. Once uniform, solvent may be used to QS the mixture if necessary.

Process parameters that may be optimized during the various mixing steps can include mix speed of side sweeps, side sweep mixing time, mix speed of homogenizer, and/or homogenizer mixing time.

In some embodiments, the mix speed of the side sweeps may be constant during the mixing process. In some embodiments, the mix speed of the side sweeps may vary during the mixing process. In some embodiments, the mix speed of side sweeps may be from 30 to 500 rpm, from 50 to 400 rpm, or from 70 to 300 rpm. In some embodiments, the mix speed of side sweeps may increase one or more times during the mixing time. In some embodiments, the mix speed of side sweeps may decrease one or more times during the mixing time. In some embodiments, the homogenizer may be on for all or part of the mixing speed time.

In some embodiments, side sweep mix time may be from 30 seconds to 6 hours, from 1 minute to 3 hours, or from 3 minutes to 2 hours. In some embodiments, the mix speed of the homogenizer may be from 5000 to 20,000 rpm, from 8,000 to 18,000 rpm, or from 10,000 to 15,000 rpm. In some embodiments, the homogenizer mixing time may be from 30 seconds to 1 hour, from 1 minute to 45 minutes, or from 5 minutes to 30 minutes. In some embodiments, the homogenizer mixing time is a subset of the side sweep mixing time, during which both the homogenizer and the side sweeper are in operation.

EXAMPLES

Example 1

Provided below in Table 2 is an example of a topical analgesic composition according to some embodiments provided herein.

| Ingredient | International Nomenclature of Cosmetic Ingredient Name | Weight percent |
| --- | --- | --- |
| Menthol Crystals USP | Menthol | 15.993 |
| Camphor Crystals USP | Camphor | 5.500 |
| Hydroxypropyl Cellulose USP-NF | Hydroxypropyl cellulose | 1.000 |
| Advantage ™ LC-A | Vinyl Caprolactam/VP/Dimethylaminoethyl Methacrylate Copolymer | 3.000 |
| Aquaflex ™ XL-30 | Polyimide-1 | 2.000 |
| Hydrolite ® 5 | Pentylene glycol | 3.000 |
| HOTACT ® VBE | Vanillyl butyl ether | 0.300 |
| Coolact ® 10 | Menthoxypropanediol | 0.900 |
| Coolact ® P | Isopulegol | 0.900 |
| Emulsifier 10 | lauryl PEG/PPG-18/19 methicone | 2.000 |
| Linseed Oil | Linseed Oil | 0.100 |
| Vitamin E | Vitamin E | 0.500 |
| Essential Oil blend | Peppermint Oil, *Eucalyptus* Oil, Rosemary Oil, Spanish Marjoram Oil, Clove Oil, Frankincense, Vitamin E | 1.000 |
| Fragrance | Mystic Sage and Minerals | 1.000 |
| Specially Denatured Alcohol 40-B 190 Proof | Ethanol | 62.867 |

Example 2

Provided below is an example of a method of preparing a topical analgesic composition according to some embodiments provided herein. The method was conducted using the ingredients and amounts provided in Table 2 immediately above.

A menthol-camphor melt was prepared by weighing and transferring the menthol and camphor into a sealed vessel. The mixture was heated in a water bath at 40° C. until a uniform colorless liquid was achieved. The mixture was removed from heat and set aside.

The alcohol (i.e., solvent) was weighed and transferred to an IKA mixer. The histamine dihydrochloride was weighed and transferred to the mixer comprising the alcohol. The mixer was turned on with both side sweeps and homogenizer. The solution was mixed with side sweeps at 90 rpm for 4 minutes and with the homogenizer at 13,000 rpm for 3 minutes (of the 4 minutes of side sweep mixing) for a total mixing time of 4 minutes. The solution was mixed until a visibly clear solution was achieved.

The hydroxypropyl cellulose was weighed and transferred to the mixer in small increments. The solution was mixed with side sweeps at 100 rpm increased to 150 rpm, increased to 200 rpm for sixty-two minutes. The solution was mixed with the homogenizer at 13,000 rpm in four different increments for a total of fifteen minutes (of the sixty-two minutes of side sweep mixing) for a total mixing time of sixty-two minutes. The solution was mixed until a visibly clear solution free from any particulate matter was achieved.

The menthol-camphor melt was reheated (if it had started to recrystallized) to form a liquid. It was then added to the mixture and mixed until a visibly clear solution was achieved. Specifically, the solution was mixed with side sweeps at 150 rpm for 4 minutes and simultaneously with the homogenizer at 13,000 rpm for 4 minutes for a total mixing time of 4 minutes.

The vinyl caprolactam/VP/dimethylaminoethyl methacrylate copolymer and polyimide-1 were weighed and added to the mixer. The polymers were mixed into solution with side sweeps at 150 rpm, increased to 160 rpm, increased to 175 rpm for a total of 4 minutes. The solution was mixed using the homogenizer at 13,000 rpm for a total of 4 minutes as well, for a total mixing time (side sweeps and homogenizer) of 4 minutes.

The sensates, pentylene glycol, emulsifier, linseed oil, vitamin E, essential oil blend, and fragrance blend were all weighed and added to the mixer. The solution was mixed until uniform. In particular, the solution was mixed with side sweeps at 175 rpm for 9 minutes and the homogenizer at 13,000 rpm for 8 minutes of the 9 minutes of side sweep mixing (for a total mix time of 9 minutes).

The solution was removed from the mixer and placed on a balance. Additional alcohol was used to QS the solution to reach the target batch size if necessary (and mixed). The solution was transferred to an air tight vessel for storage.

Example 3

A topical analgesic composition according to embodiments provided herein was microscopically analyzed to characterize the film-forming encapsulating matrix. In particular, FIG. 2 shows an image of a topical analgesic composition magnified 4000×. The figure shows that the active ingredients (e.g., menthol, camphor), the sensates, and the essential oils form tiny droplets within the topical analgesic composition. These nano-sized droplets are dispersed and stabilized in a film-forming matrix comprising the polymer system and the solvent (i.e., alcohol). These nano-sized droplets may mitigate coalescence. As discussed above, the encapsulating film-forming matrix that traps the active ingredients, sensates, and essential oils can lead to faster absorption through the skin. Faster absorption through the skin can reduce the amount of time between application and the onset of the therapeutic effect (e.g., pain relief). Faster absorption into the skin can also lead to easier spreadability of the topical analgesic composition into the skin. Once the topical analgesic composition is spread onto the skin, the alcohol solvent begins to evaporate. Evaporation of the alcohol solvent results in evenly-dispersed nano-sized droplets throughout the encapsulating film-forming matrix.

FIG. 3 shows a droplet size analysis of the magnified topical analgesic composition. As shown in the figure, the average droplet size is 0.79 microns (790 nm), the maximum droplet size is 2.07 microns, and the minimum droplet size is 0.0 microns. Thus, this topical analgesic composition can be characterized as a stable nano-encapsulating matrix film holding the droplets together (once the primary alcohol solvent evaporates) due to the uniform droplet size distribution and the lack coalescence.

FIGS. 2 and 3 were captured using a VHX 5000 digital microscope (Keyence Corp. America, NJ, USA) and Version 1.4 of the corresponding software. The image was captured by taking a neat sample of a topical analgesic formulation and spreading it thinly on a glass slide. The glass slide with the spread sample was placed under the microscope in light transmittance mode with a magnification factor of 2000×. The image was then digitally analyzed using an automatic area extraction algorithm based upon pixel density.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X".

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A topical analgesic composition comprising:
   12 to 16 wt. % menthol;
   4 to 8 wt. % camphor;
   2 to 15 wt. % film-forming polymer comprising hydroxypropyl cellulose; and
   50 to 70 wt. % an alcohol solvent,
   wherein the topical analgesic composition has a viscosity from 800 to 1400 centipoise and comprises:
      a film-forming matrix comprising the film-forming polymer and the alcohol solvent; and
      droplets comprising the menthol and the camphor, wherein the droplets are dispersed in the film-forming matrix, and wherein the droplets have an average droplet size of 800-1500 nanometers.

2. The composition of claim 1, further comprising 0.025 to 0.250 wt. % histamine dihydrochloride.

3. The composition of claim 1, wherein the amount of menthol and the amount of camphor comprises 21 wt. % of the composition.

4. The composition of claim 1, having a pH from 6.0 to 7.0.

5. The composition of claim 1, having a specific gravity from 0.7 to 1.0.

6. The composition of claim 1, wherein the 2 to 15 wt. % film-forming polymer further comprises one or more of a terpolymer of vinylpyrrolidone, vinyl caprolactum and dimethylaminoethyl methacrylate, and a terpolymer of poly(isobutylene-alt-maleic anhydride), dimethylaminopropylamine, and methoxy-PEG/PPG-31/9-2-propylamine.

7. The composition of claim 1, wherein the 12 to 16 wt. % menthol and the 5-10 wt. % camphor form a eutectic mixture.

8. The composition of claim 1, further comprises 1.5 to 9 wt. % sensate.

9. The composition of claim 8, wherein the sensate includes one or more of menthoxypropanediol, isopulegol, and vanillyl butyl ether.

10. The composition of claim 1, further comprises 0.5 to 3.0 wt. % of one or more essential oils.

11. The composition of claim 10, wherein the one or more essential oils comprises one or more of peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil, and frankincense (*Olibanum* or *Boswellia carterii*) oil.

12. The composition of claim 1, further comprises 0.1 to 5 wt. % linseed oil.

13. The composition of claim 1, further comprises 0.5 to 3.0 wt. % fragrance.

14. A method for treating muscle and joint ache or pain, comprising administering to a patient in need thereof a topical analgesic composition according to claim 1.

15. A roll-on topical analgesic product comprising:
   a roll-on applicator; and
   a topical analgesic composition comprising:
      12 to 16 wt. % menthol;
      4 to 8 wt. % camphor;
      2 to 15 wt. % film-forming polymer comprising hydroxypropyl cellulose; and
      50 to 70 wt. % an alcohol solvent,
   wherein the topical analgesic composition has a viscosity from 800 to 1400 centipoise contained within the roll-on applicator to form a roll-on topical analgesic product and comprises:
      a film-forming matrix comprising the film-forming polymer alcohol and the solvent; and
      droplets comprising the menthol and the camphor, wherein the droplets are dispersed in the film-forming matrix, and wherein the droplets have an average droplet size of 800-1500 nanometers.

16. A method of preparing a topical analgesic composition, the method comprising:
   mixing 12 to 16 wt. % menthol and 4 to 8 wt. % camphor; and
   adding 50 to 70 wt. % of an alcohol a solvent and 2 to 15 wt. % of a film-forming polymer comprising hydroxypropyl cellulose to the mixture comprising said menthol and said camphor to form a topical analgesic composition wherein the topical analgesic composition has a viscosity from 800 to 1400 centipoise and comprises: a film-forming matrix comprising the film-forming polymer and the alcohol solvent; and droplets comprising the menthol and the camphor, wherein the droplets are dispersed in the film-forming matrix, and wherein the droplets have an average droplet size of 800-1500 nanometers.

17. The method of claim 16, wherein the topical analgesic composition has a pH of 6.0-7.0.

18. The composition of claim 1, wherein an amount of camphor in the composition is 5 to 8 wt. %.

* * * * *

UNITED STATES PATENT AND TRADEMARK OFFICE
CERTIFICATE OF CORRECTION

PATENT NO. : 12,097,186 B2
APPLICATION NO. : 16/856363
DATED : September 24, 2024
INVENTOR(S) : Das et al.

It is certified that error appears in the above-identified patent and that said Letters Patent is hereby corrected as shown below:

In the Claims

In Column 24, Line 23, Claim 15, delete "polymer alcohol and the" and insert -- polymer and the alcohol --, therefor.

Signed and Sealed this
Eighth Day of April, 2025

Coke Morgan Stewart
*Acting Director of the United States Patent and Trademark Office*